United States Patent
Ito

(10) Patent No.: US 7,336,894 B2
(45) Date of Patent: Feb. 26, 2008

(54) ELECTRONIC ENDOSCOPE SYSTEM, LIGHTING DEVICE FOR ELECTRONIC ENDOSCOPE SYSTEM, AND LIGHT CONTROLLER FOR ELECTRONIC ENDOSCOPE SYSTEM

(75) Inventor: Shunichi Ito, Tokyo (JP)

(73) Assignee: PENTAX Corporation, Tokyo (JP)

( * ) Notice: Subject to any disclaimer, the term of this patent is extended or adjusted under 35 U.S.C. 154(b) by 380 days.

(21) Appl. No.: 11/091,627

(22) Filed: Mar. 29, 2005

(65) Prior Publication Data

US 2005/0220447 A1    Oct. 6, 2005

(30) Foreign Application Priority Data

Mar. 31, 2004    (JP)    .............................. 2004-103941

(51) Int. Cl.
- G03B 29/00    (2006.01)
- G03B 9/20     (2006.01)
- A61B 1/04     (2006.01)
- A61B 1/06     (2006.01)

(52) U.S. Cl. .................. 396/17; 396/497; 600/180; 348/68

(58) Field of Classification Search .................. 396/17, 396/493, 497; 600/180; 348/68–69; 362/16, 362/18, 109

See application file for complete search history.

(56) References Cited

U.S. PATENT DOCUMENTS

| 4,729,018 | A |   | 3/1988 | Watanabe et al. ............. 348/69 |
| 4,740,837 | A |   | 4/1988 | Yanagisawa et al. ......... 348/68 |
| 5,642,456 | A | * | 6/1997 | Baker et al. ................. 385/140 |
| 2006/0088303 | A1 | * | 4/2006 | Ito ............................... 396/17 |

FOREIGN PATENT DOCUMENTS

| JP | 62-69222 | 3/1987 |
| JP | 7-85132  | 9/1995 |

* cited by examiner

*Primary Examiner*—Christopher Mahoney
(74) *Attorney, Agent, or Firm*—Greenblum & Bernstein, P.L.C.

(57) ABSTRACT

A lighting device for an electronic endoscope system, includes a light source; a set of rotary shutters having at least two rotary shutters, having a rotational axis parallel to an optical axis of the light source, the rotary shutters alternately intercepting incident illuminating light emitted from the light source and allowing the incident illuminating light to pass through the set of rotary shutters to proceed toward a light guide, wherein the rotary shutters are associated with each other to be capable of integrally rotating about the rotational axis, each of the rotary shutters having at least one light-shielding portion and at least one opening; and an adjusting device which rotates one of the rotary shutters relative to the other to change an opening angle of each opening to adjust an amount of illuminating light which passes through the set of rotary shutters.

15 Claims, 5 Drawing Sheets

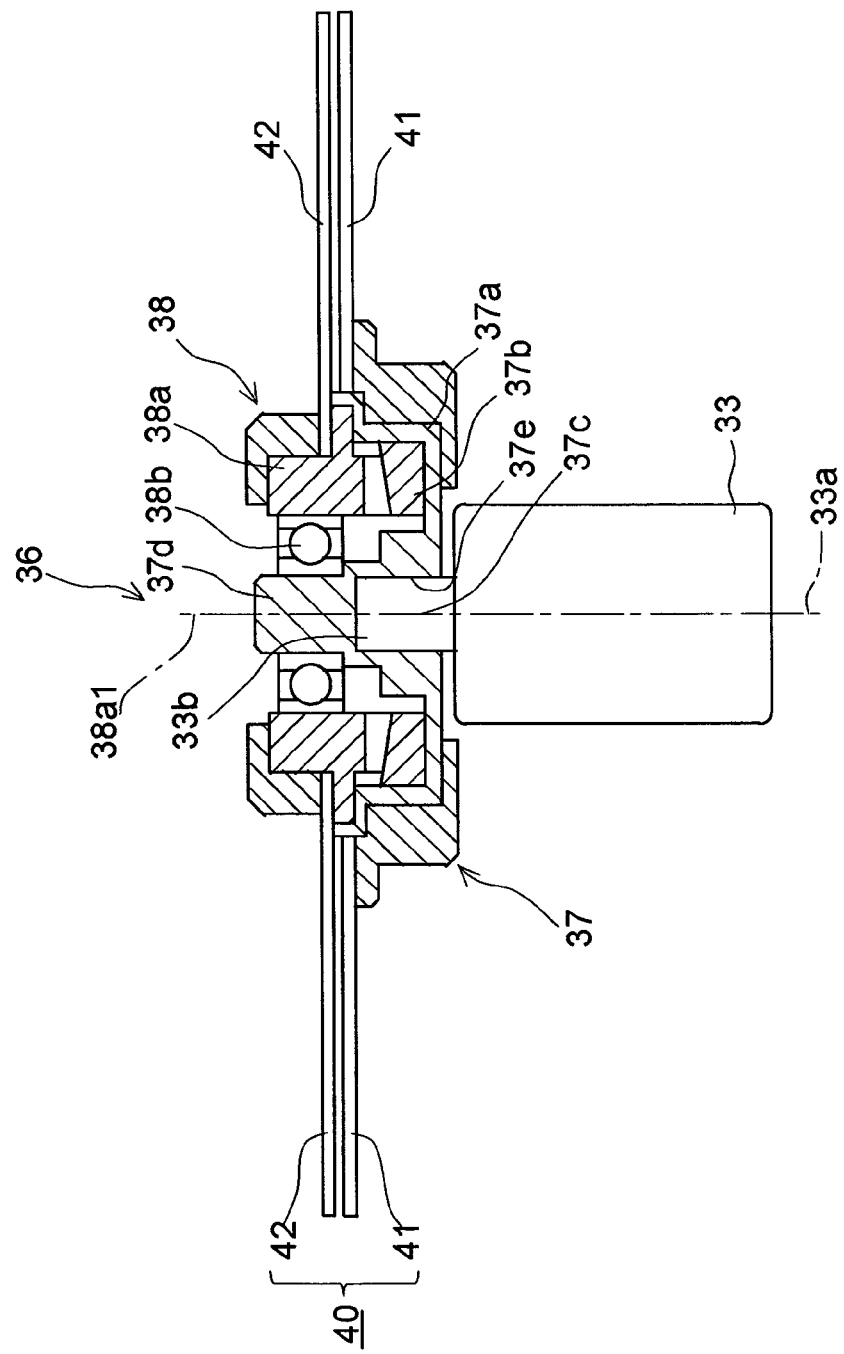

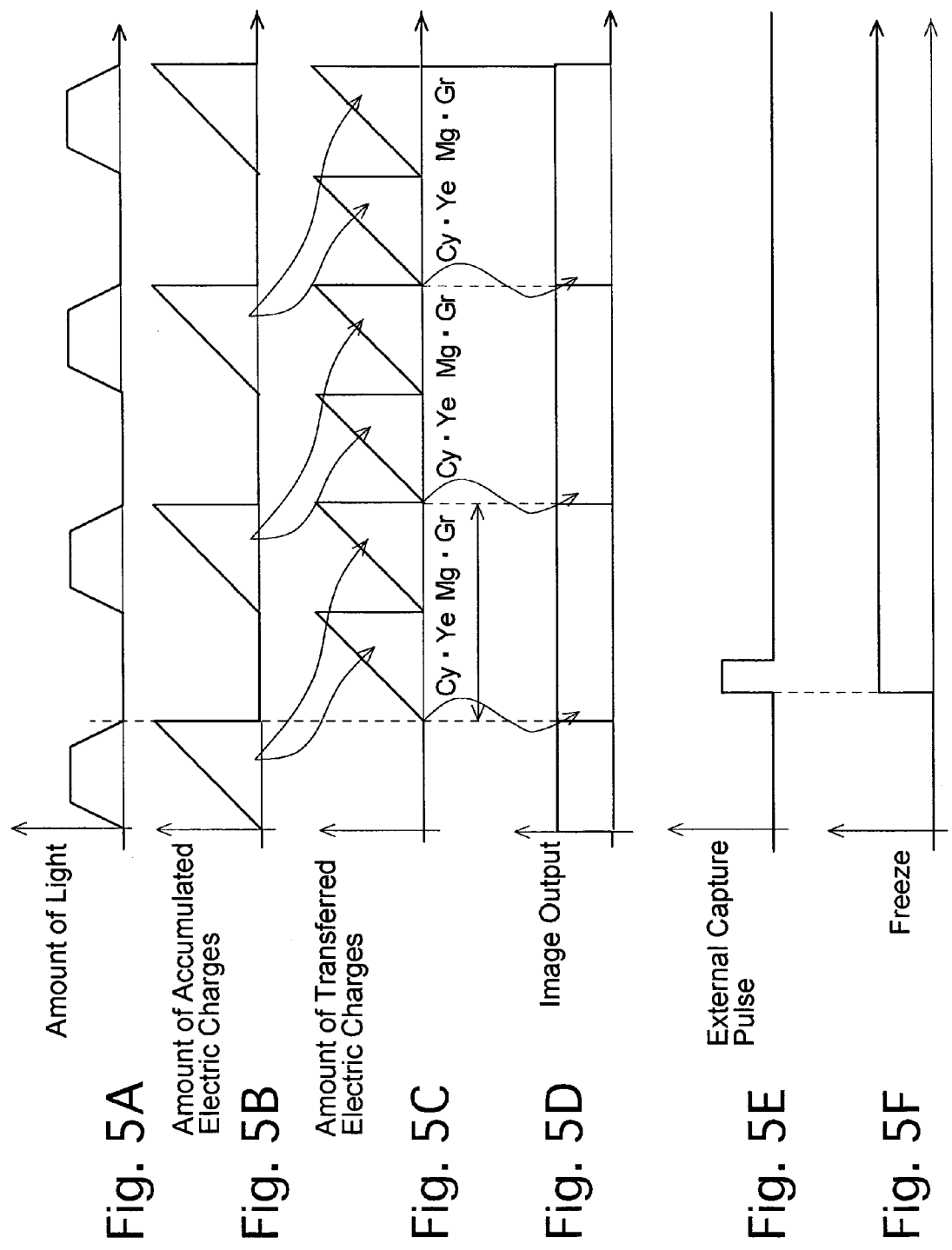

1

ELECTRONIC ENDOSCOPE SYSTEM, LIGHTING DEVICE FOR ELECTRONIC ENDOSCOPE SYSTEM, AND LIGHT CONTROLLER FOR ELECTRONIC ENDOSCOPE SYSTEM

BACKGROUND OF THE INVENTION

1. Field of the Invention

The present invention relates to an electronic endoscope system, more specifically relates to a lighting device for an electronic endoscope system using more than one rotary shutter, and also a light controller device for such an electronic endoscope system using more than one rotary shutter.

2. Description of the Related Art

In conventional electronic endoscope systems, an endoscopic recording device designed to make an appropriate lighting control possible has been proposed in Japanese laid-open patent publication S62-69222. This endoscopic recording device includes a rotary shutter having a rotational axis the position of which is adjustable relative to an optical axis of a lighting device of the endoscope system; i.e., the distance between the rotational axis and an optical axis of the lighting device is adjustable. The rotary shutter is shaped so that a peripheral speed (peripheral velocity) varies at different points in a radial direction when the rotary shutter rotates (or so that an open area ratio varies at different points on the rotary shutter when the rotary shutter rotates). With the variations in peripheral speed, the amount of light emitted from a light source of the lighting device is adjusted by changing the distance between the axis of the rotational axis and the optical axis of the lighting device.

Although lighting control is possible in the above noted conventional endoscopic recording device disclosed in Japanese laid-open patent publication S62-69222, the structure of the rotary shutter is complicated. Specifically, providing such a conventional endoscopic recording device with a mechanism for changing the distance between the rotational axis and the optical axis of the lighting device is essential, which is costly and troublesome. Additionally, in order to embody this structure, the outer diameter of the rotary shutter has to be several times larger than the diameter of the light bundle of the incident light on the incident end face of a fiber-optic light guide (a bundle of fibers) of the endoscope, which inevitably increases the size of the rotary shutter. On the other hand, if the rotary shutter is formed in an asymmetrical shape with respect to the rotational axis thereof so that an open area ratio changes at different points on the rotary shutter when the rotary shutter rotates, the rotational center of the rotary shutter is not coincident with the center of gravity of the rotary shutter, so that the rotary shutter may lose balance during rotation, and accordingly there is a possibility of the illuminating light which emerges from the exit end face of the fiber-optic light guide becoming unwanted illuminating light, and there is a possibility of the rotary shutter and peripheral components thereof being damaged.

SUMMARY OF THE INVENTION

The present invention provides an electronic endoscope system incorporating a set of small-diameter rotary shutters which do not require a mechanism for changing the distance between the rotational axis of the set of rotary shutters and the optical axis of a lighting device of the electronic endoscope system, and which is capable of rotating while the set of rotary shutters remain in balance. The present invention also provides a lighting device for an electronic endoscope system which incorporates such a set of rotary shutters, and further provides a light controller, used for an electronic endoscope system, using such a set of rotary shutters for controlling the amount of illuminating light which passes through the set of rotary shutters.

According to an aspect of the present invention, a lighting device for an electronic endoscope system is provided, including a light source; a set of rotary shutters having at least two rotary shutters, having a rotational axis parallel to an optical axis of the light source, the rotary shutters alternately intercepting incident illuminating light emitted from the light source and allowing the incident illuminating light to pass through the set of rotary shutters to proceed toward a light guide, wherein the rotary shutters are associated with each other to be capable of integrally rotating about the rotational axis, each of the rotary shutters having at least one light-shielding portion and at least one opening; and an adjusting device which rotates one of the rotary shutters relative to the other of the rotary shutters to change an opening angle of each the opening to adjust an amount of the illuminating light which passes through the set of rotary shutters.

It is desirable for the lighting device to include a first motor for integrally rotating the set of rotary shutters. The adjusting device includes a second motor for rotating the one of the rotary shutters relative to the other of the rotary shutters.

It is desirable for the second motor to be an ultrasonic motor.

In an embodiment, a light controller for an electronic endoscope system is provided, including a set of rotary shutters having at least two rotary shutters, having a rotational axis parallel to an optical axis of a light source, the rotary shutters alternately intercepting incident illuminating light emitted from the light source and allowing the incident illuminating light to pass through the set of rotary shutters to proceed toward a light guide, wherein the rotary shutters are associated with each other to be capable of integrally rotating about the rotational axis, each of the rotary shutters having at least one light-shielding portion and at least one opening; and an adjusting device which rotates one of the rotary shutters relative to the other of the rotary shutters to change an opening angle of each the opening to adjust an amount of the illuminating light which passes through the set of rotary shutters.

It is desirable for the lighting device to include a first motor for integrally rotating the set of rotary shutters, and for the adjusting device to include a second motor for rotating the one of the rotary shutters relative to the other of the rotary shutters.

It is desirable for the second motor to be an ultrasonic motor.

In an embodiment, an electronic endoscope system is provided, including a control portion which is manually operated by an operator; an insertion portion which extends from the control portion to be inserted into an internal cavity of a subject to be inspected; a light guide which extends through the control portion and the insertion portion so that an end of the light guide extends to a distal end of the insertion portion; and a lighting device for supplying illuminating light to the light guide. The lighting device includes a light source which emits the illuminating light; a set of rotary shutters having at least two rotary shutters, having a rotational axis parallel to an optical axis of the light source, the rotary shutters alternately intercepting incident illuminating light emitted from the light source and allowing the incident illuminating light to pass through the set of rotary shutters to proceed toward the light guide, wherein the rotary shutters are associated with each other to be capable of integrally rotating about the rotational axis, each of the rotary shutters having at least one light-shielding portion and at least one opening; and an adjusting device which rotates one of the rotary shutters relative to the other of the rotary shutters to change an opening angle of each the opening to adjust an amount of the illuminating light which passes through the set of rotary shutters.

It is desirable for the lighting device to include a first motor for integrally rotating the set of rotary shutters, and the adjusting device includes a second motor for rotating the one of the rotary shutters relative to the other of the rotary shutters.

It is desirable for the second motor to be an ultrasonic motor.

It is desirable for each of said the rotary shutters to have two light-shielding portion and two opening and for the opening angle to be changeable within a range of zero to 90 degrees.

It is desirable for rotational axes of the first motor and the second motor to be coaxially arranged.

It is desirable for each of the rotary shutters to include a central disc portion, and two rotationally-symmetrical arc-shaped light-shielding portions and two rotationally-symmetrical arc-shaped cutout portions which are arranged at equi-angular intervals about a rotational axis of the each rotary shutter.

The present disclosure relates to subject matter contained in Japanese Patent Application No. 2004-103941 (filed on Mar. 31, 2004) which is expressly incorporated herein by reference in its entirety.

BRIEF DESCRIPTION OF THE DRAWINGS

The present invention will be described below in detail with reference to the accompanying drawings in which:

FIG. 4 is a side elevational view, partly in cross section, of a portion of the lighting device shown in FIG. 1, showing the configuration of the set of rotary shutters shown in FIG. 3A, a motor and an ultrasonic motor; and FIGS. 5A through 5F are timing charts for various operations in an image capturing operation of the electronic endoscope system shown in FIGS. 1 and 2.

DESCRIPTION OF THE PREFERRED EMBODIMENT

Figure 1:
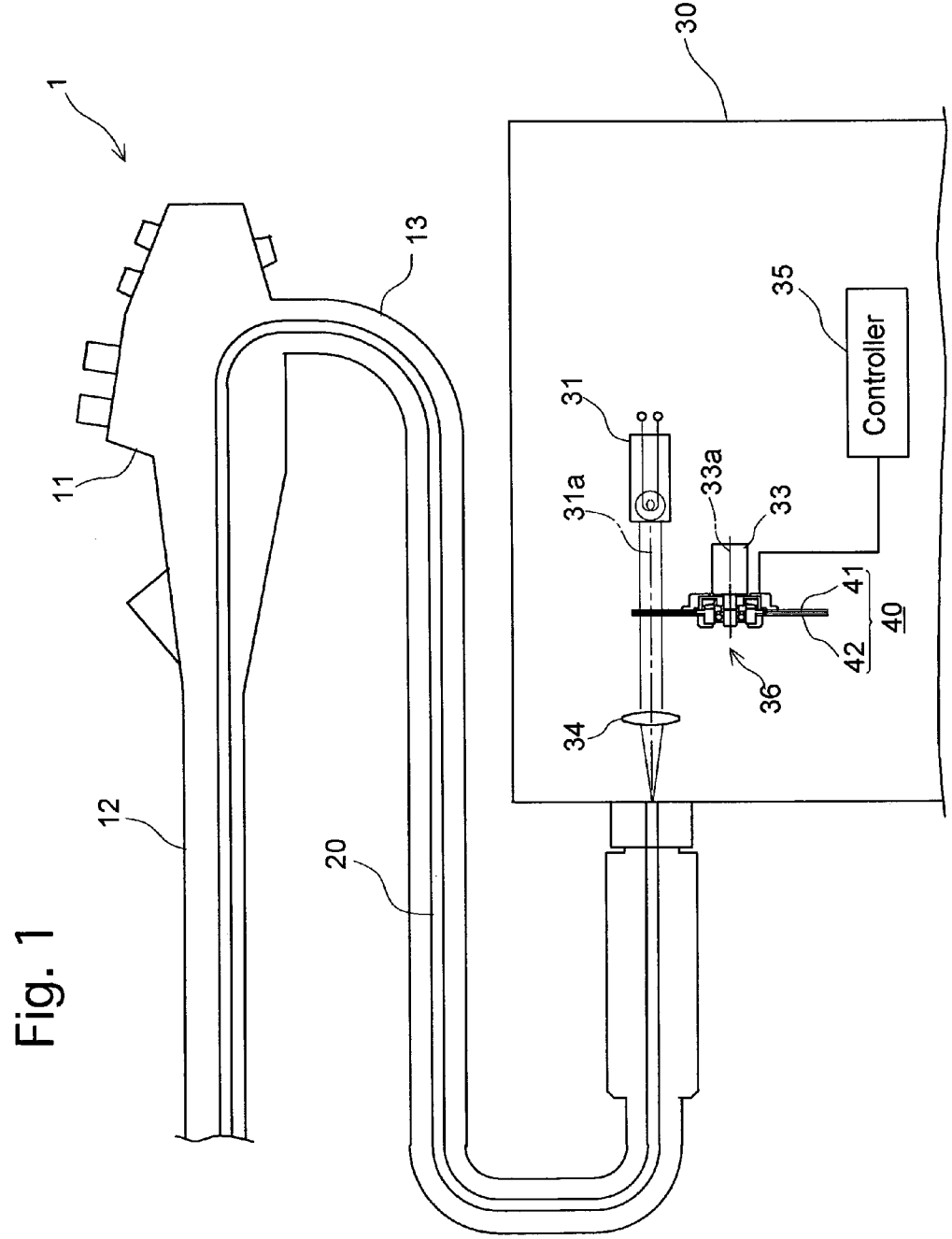
FIG. 1 is a schematic diagram of an embodiment of an electronic endoscope system including an electronic endoscope and a lighting device, according to the present invention, showing the internal structure thereof.
Figure 2:
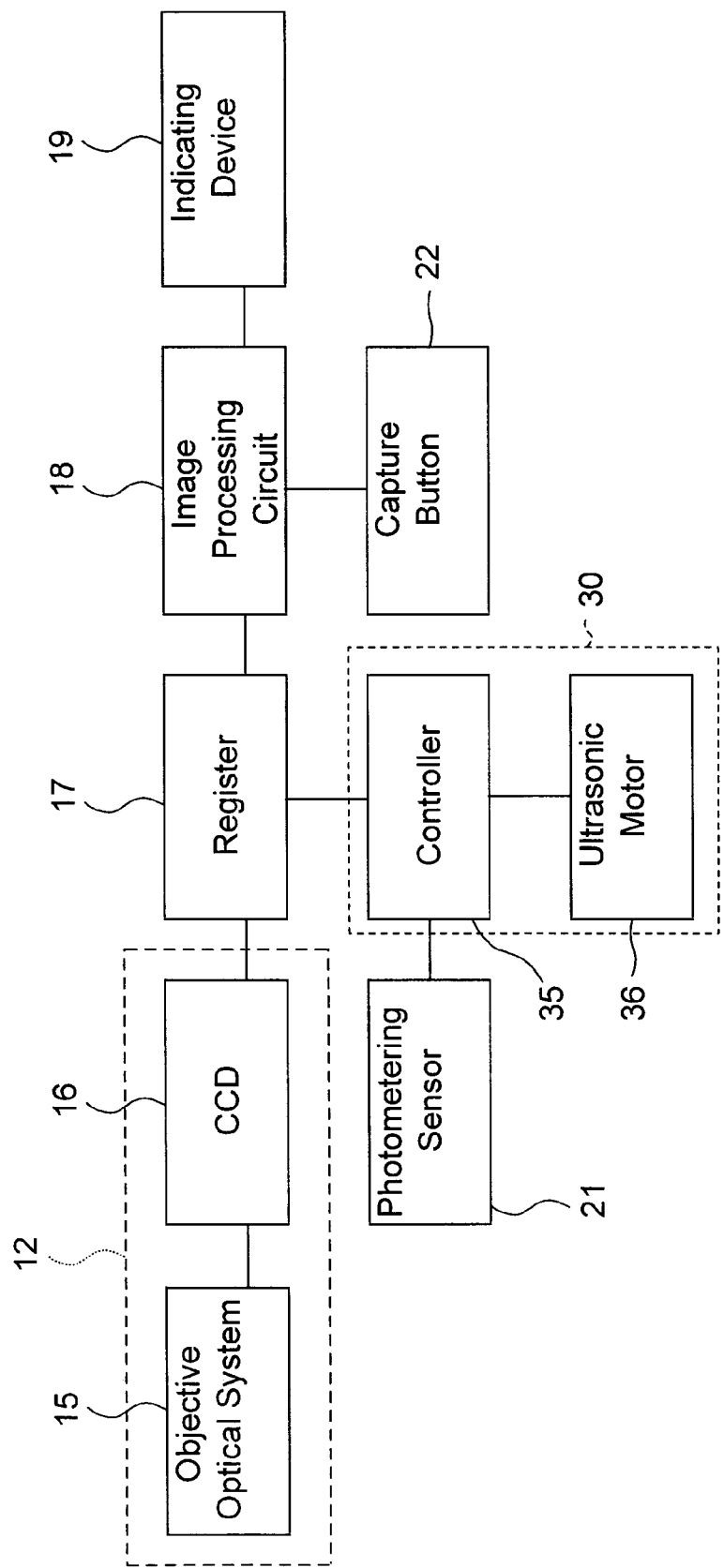
FIG. 2 is a block diagram showing the structure of the electronic endoscope system.

As shown in FIG. 1, an embodiment of an electronic endoscope system 1 is provided with a control portion 11, a flexible insertion portion (flexible insertion tube) 12, a fiber-optic light guide 20 and a lighting device 30. The control portion 11 is manually held by an operator of the electronic endoscope system 1. The flexible insertion portion 12 in the shape of a narrow tube extends from the control portion 11. The light guide 20 is connected at one end thereof to the lighting device 30 to guide illuminating light emitted from the lighting device 30 to the other end of the light guide 20 (the distal end of the flexible insertion portion 12) so that the illuminating light emerges from the distal end of the flexible insertion portion 12. The lighting device 30 is connected to the control portion 11 via an universal tube 13. The light guide 20 is inserted into the flexible insertion portion 12, the control portion 11 and the universal tube 13 to be connected to the lighting device 30. The lighting device 30 is provided therein with a lamp (light source) 31. Illuminating light emitted from the lamp 31 passes through the light guide 20 to be emerged from the distal end of the flexible insertion portion 12. The illuminating light which is emitted from the lamp 31 to be eventually incident on an observation area is reflected thereby partly enters back into the flexible insertion portion 12 through an objective optical system 15 to be incident on a CCD image sensor (solid-state image pick-up device) 16 to be accumulated thereby as electric charges (see FIG. 2). The objective optical system 15 and the CCD image sensor 16 constitute an imaging device. The CCD image sensor 16 is an interlace CCD image sensor which divides one frame into an even field (even field lines) and an odd field (odd field lines). All pixel data are divided into an even field and an odd field to be transferred to a register (image data accumulating device) 17, and subsequently the even field and the odd field which are transferred to the register 17 are decompressed into one frame by an image processing device 18 which is connected to the register 17 to be visually indicated on an indicating device 19 (see FIG. 2), e.g., a display monitor.

In addition to the lamp 31, the lighting device 30 is provided with a set of rotary shutters 40, a converging lens 34, a motor (first motor) 33 and an ultrasonic motor (second motor/adjusting device) 36. The set of rotary shutters 40 has a rotational axis 40b parallel to an optical axis 31a of the lamp 31, and is capable of controlling and intercepting the illuminating light which is emitted by the lamp 31 to proceed toward the converging lens 34. The converging lens 34 converges the incident illuminating light onto the proximal end of the light guide 20 to lead the illuminating light into the light guide 20. The set of rotary shutters 40 is composed of two independent rotary shutters: a first rotary shutter 41 and a second rotary shutter 42. The motor 33 integrally rotates the set of rotary shutters 40 about the rotational axis 40b, and the ultrasonic motor 36 rotates the second rotary shutter 42 about the rotational axis 40b relative to the first rotary shutter 41.

Figure 3A:
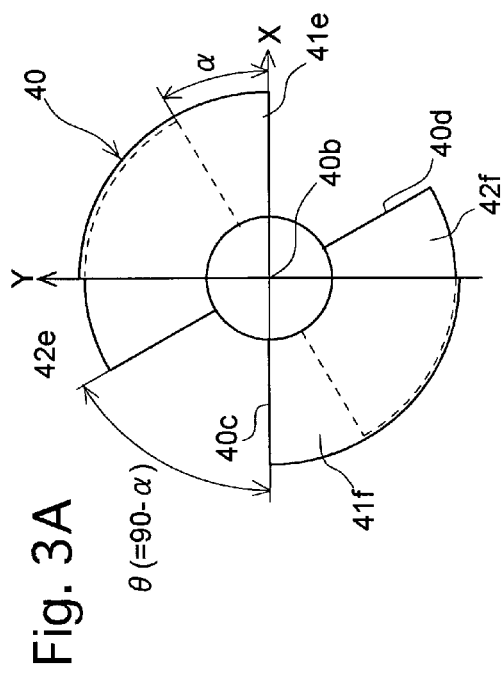
FIG. 3A is a plan view of a first rotary shutter and a second rotary shutter which are joined together to be capable of rotating relative to each other about a common rotational axis.
Figure 3C:
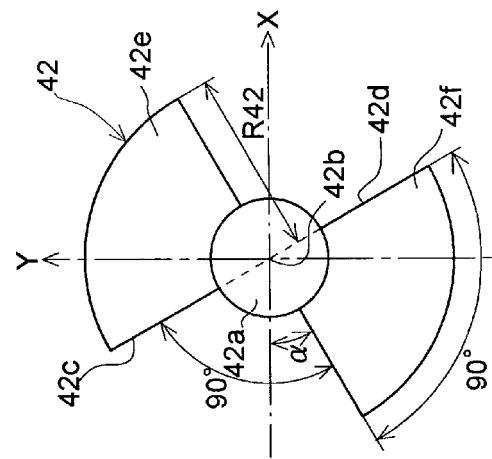
FIG. 3C is a plan view of the second rotary shutter shown in FIG. 3A.
Figure 3B:
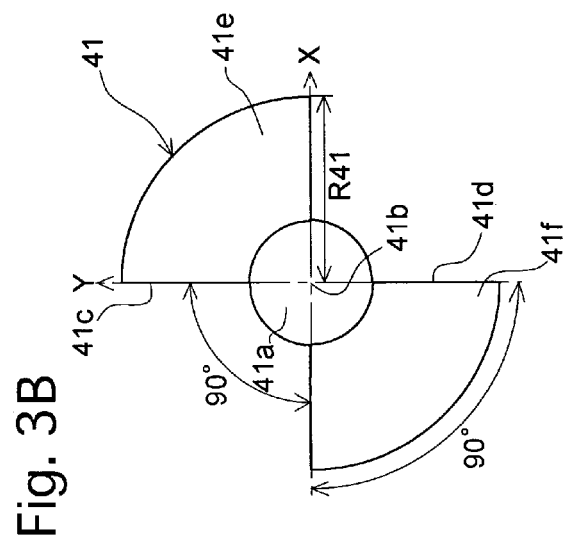
FIG. 3B is a plan view of the first rotary shutter show in FIG. 3A.

As shown in FIGS. 3B and 3C, the first rotary shutter 41 and the second rotary shutter 42 have the same shape. The first rotary shutter 41 is molded from aluminum and has a radius R41 as shown in FIG. 3B. The first rotary shutter 41 is provided at the center thereof with a disc portion 41a with its center on the rotational axis 41b, and is further provided with two rotationally-symmetrical arc-shaped light-shielding portions 41e and 41f and two rotationally-symmetrical arc-shaped cutout portions 41c and 41d which are arranged at equi-angular intervals of 90 degrees about the rotational axis 41b. The first rotary shutter 41 is shaped in a manner so as to have the arc-shaped cutout portions 41c and 41d cut out from a whole disc having the radius R41 without a central portion (the disc portion 41a) of the disc being cut out.

Similarly, the second rotary shutter 42 that is shown in FIG. 3C is molded of aluminum and has a radius R42 which is slightly smaller than the radius R41 of the first rotary shutter 41 (R42<R41). Similar to the first rotary shutter 41, the second rotary shutter 42 is provided at the center thereof with a disc portion 42a with its center on the rotational axis 42b, and is further provided with two rotationally-symmetrical arc-shaped light-shielding portions 42e and 42f and two rotationally-symmetrical arc-shaped cutout portions 42c and 42d which are arranged at equi-angular intervals of 90 degrees about the rotational axis 42b. The second rotary shutter 42 is shaped in a manner so as to have the two arc-shaped cutout portions 42c and 42d cut out from a whole disc having the radius R42 without a central portion (the disc portion 42a) of the disc being cut out. Each of the radius R41 and the radius R42 is desirably equal to or greater than the diameter of the bundle of illuminating light which is emitted from the lamp 31 and incident on the set of rotary shutters 40. If this condition is satisfied, the radius R41 can be equal to the radius R42 (R41=R42) or smaller than the radius R42 (R41<R42). In addition, in each of the first and second rotary shutters 41 and 42, each of the two arc-shaped light-shielding portions (41e and 41f, 42e and 42f) can be formed to have a central angle other than 90 degrees; namely, each of the two arc-shaped cutout portions (41c and 41d, 42c and 42d) can be formed to have a central angle other than 90 degrees. Additionally, the shapes of the first rotary shutter 41 and the second rotary shutter 42 can be mutually different. Moreover, the set of rotary shutters 40 can be constructed so as to have more than two rotary shutters.

The first rotary shutter 41 and the second rotary shutter 42 that are formed in the above described manner are connected to each other so as to be capable of rotating relative to each other with the rotational axes 41b and 42b coincident with each other. The first rotary shutter 41 is positioned so that the two arc-shaped light-shielding portions 41e and 41f respectively lie within the first quadrant (upper right quadrant) and the third quadrant (lower left quadrant) of a plane having X and Y coordinates. If the second rotary shutter 42 is positioned so that the two arc-shaped light-shielding portions 42e and 42f thereof do not overlap the two arc-shaped light-shielding portions 41e and 41f of the first rotary shutter 41, respectively, by an angle of $\alpha$ degrees in a counterclockwise direction as shown in FIG. 3A, the two arc-shaped cutout portions 41c and 41d of the first rotary shutter 41 are partly shut by the two arc-shaped light-shielding portions 42e and 42f of the second rotary shutter 42, respectively. Due to this structure, two openings 40c and 40d of the set of rotary shutters 40, which are respectively formed by the two arc-shaped cutout portions 41c and 42c and the two arc-shaped cutout portions 41d and 42d, are rotationally symmetrical with respect to the rotational axis 40b of the set of rotary shutters 40, and accordingly, have the same arc shape having a central angle (opening angle) of $\theta$ degrees ($\theta$=90 degrees–$\alpha$ degrees). The angle $\theta$ can be adjusted in a range from zero to 90 degrees by rotating the second rotary shutter 42 about the rotational axis 40b relative to the first rotary shutter 41 by the ultrasonic motor 36. If the angle $\theta$ is set to zero, the set of rotary shutters 40 fully prevents the incident illuminating light from passing therethrough.

As shown in FIG. 4, the set of rotary shutters 40, which consists of the first rotary shutter 41 and the second rotary shutter 42, is fixed to the ultrasonic motor 36 that can rotate the second rotary shutter 42 relative to the first rotary shutter 41. More specifically, the first rotary shutter 41 is bonded to a base 37a of a stator 37 of the ultrasonic motor 36, while the second rotary shutter 42 is bonded to a cylindrical portion 38a of a rotor 38 of the ultrasonic motor 36. The base 37a concentrically extends through the disc portion 41a of the first rotary shutter 41, while the cylindrical portion 38a concentrically extends through the disc portion 42a of the second rotary shutter 42. In addition to the cylindrical portion 38a, the rotor 38 of the ultrasonic motor 36 is provided with a ring-shaped ball bearing 38b, the cylindrical outer peripheral surface of which is fixed to a cylindrical inner peripheral surface of the cylindrical portion 38a. The stator 37 is provided with an array of piezoelectric elements 37b in the shape of a ring which is fitted into the base 37a to be able to be in contact with the cylindrical portion 38a. Due to this structure, feeding a current through the array of piezoelectric elements 37b causes the array of piezoelectric elements 37b to be deformed in accordance with the amount of electrical current, thus causing the cylindrical portion 38a of the rotor 38 to rotate about a rotational axis 38a1 thereof in accordance with the deformation of the array of piezoelectric elements 37b, so that the second rotary shutter 42 rotates relative to the first rotary shutter 41. On the other hand, in a state where no current is fed through the array of piezoelectric elements 37b, the first rotary shutter 41 and the second rotary shutter 42 integrally rotate together if the first rotary shutter 41 is rotated.

The stator 37 is provided along an axis thereof with a rotating-shaft insertion hole 37e which extends along a rotational axis 37c of the stator 37. A rotary shaft 33b of the motor 33 (e.g., a DC motor or an AC motor) is fitted into the rotating-shaft insertion hole 37e to be firmly fixed thereto by a bonding agent with a rotational axis 33a of the motor 33 coincident with the rotational axis 37c of the stator 37. Due to this structure, driving the motor 33 causes the stator 37 and the first rotary shutter 41 to rotate about the rotational axes 37c and 41b, respectively. At this time, the second rotary shutter 42 integrally rotates together with the first rotary shutter 41 if no current is applied to the array of piezoelectric elements 37b, or the second rotary shutter 42 rotates relative to the first rotary shutter 41 by an amount of rotation corresponding to the duration or amount of current applied to the array of piezoelectric elements 37b if a current is applied to the array of piezoelectric elements 37b. Accordingly, the opening angle $\theta$ of each of the two openings 40c and 40d of the set of rotary shutters 40 can be varied to adjust the amount of the illuminating light which emerges from the set of rotary shutters 40 toward the converging lens 34 by rotating the second rotary shutter 42 relative to the first rotary shutter 41 by applying a current for a predetermined period of time or a predetermined amount of current to the array of piezoelectric elements 37b during rotation of the first rotary shutter 41 by the motor 33. This makes it possible to control the illuminating light. The current applied to the array of piezoelectric elements 37b is controlled by a controller (adjusting device) 35 provided in the lighting device 30.

An actual image capturing operation for capturing images of an observation area will be hereinafter discussed with reference to FIGS. 5A through 5F. Prior to performing the image capturing operation, the insertion portion 12 is inserted into an internal body cavity of a patient (or an internal cavity inside a machine, etc.), and the distal end of the insertion portion 12 is directed to an observation area. In this state, pressing a start button (not shown) causes the lamp 31 to be turned ON so that the lamp 31 emits illuminating light, thus causing the observation area to be illuminated via the light guide 20 so that the observation area is visually indicated on the indicating device 19. During this indicating operation, the brightness of the observation area is monitored by a photometering sensor 21, and the second rotary shutter 42 is rotated relative to the first rotary shutter 41 by the controller 35 in a manner such that the central angle (opening angle) θ of each of the two openings 40c and 40d is 90 degrees or closer to 90 degrees as the brightness of the observation area is lower, and the central angle θ of each of the two openings 40c and 40d becomes closer to zero degrees as the brightness of the observation area is higher.

FIGS. 5A through 5F show the timings of the amount of illuminating light emitted toward an observation area, the amount of accumulated electric charges to the CCD image sensor 16, the amount of electric charges transferred to the register 17 and an image outputting operation, respectively, on condition that the brightness of the observation area is constant. These timings do not change even if the brightness of the observation area is not constant.

The set of rotary shutters 40 is rotated one revolution per 1/30 second (i.e., at 1800 rpm), and the illuminating light emitted from the lamp 31 emerges from the set of rotary shutters 40 toward the converging lens 34 by a period of time per revolution (lighting duration) which corresponds to the opening angle θ of each of the two openings 40c and 40d. For instance, if the opening angle θ is 90 degrees, the illuminating light emerges from the set of rotary shutters 40 toward the converging lens 34 for 1/120 second through the opening 40c and for another 1/120 second through the opening 40d per revolution of the set of rotary shutters 40, and the illuminating light emitted from the lamp 31 is intercepted by the set of rotary shutters 40 so as not to be incident on the converging lens 34 for the remaining total time (light-shielding duration) of 1/60 second per revolution of the set of rotary shutters 40. For instance, if the opening angle θ of each opening 40c and 40d is 90 degrees, the lighting duration of 1/120 second and the light-shielding duration of 1/120 second alternately occur two times per revolution of the set of rotary shutters 40 (see FIG. 5A). Accordingly, desired images can be obtained if the set of rotary shutters 40 is rotated at half speed of a normal frame rate (e.g., 30 fps). The illuminating light which is reflected by an observation area to be incident on the CCD image sensor 16 is accumulated as electric charges to the CCD image sensor 16 which are divided into an odd field (corresponding to cyan pixel data and yellow pixel data in this particular embodiment) and an even field (corresponding to magenta pixel data and green pixel data in this particular embodiment) every 1/30 second with the odd field and the even field being sequentially accumulated (see FIG. 5B). Because the odd field and the even field are sequentially accumulated, the possibility of the occurrence of a blurred image decreases when the odd field and the even field are combined to form an image frame afterwards.

During the light-shielding duration following the lighting duration of either opening 40c or 40d, pixel data on the odd field are transferred to the register 17 from the CCD image sensor 16 (see FIG. 5C). This data transfer operation commences when it is detected, using a photometering sensor 21 (see FIG. 2) connected to the controller 35, that the illuminating light emitted from the lamp 31 is intercepted by the set of rotary shutters 40, and when the controller 35 outputs a command signal which instructs the CCD image sensor 16 to start transferring pixel data on the odd field to the register 17 in accordance with the aforementioned detection using the photometering sensor 21.

Upon completion of the operation transferring pixel data on the odd field to the register 17, pixel data on the even field commences to be transferred to the register 17. On the other hand, the lighting duration starts again upon completion of the light-shielding duration. Although this lighting duration and the even-field pixel data transferring operation commence at the same time, the accumulation of the even field is renewed after the previous pixel data on the even field has been transferred to the register 17 because the accumulating operation to the CCD 16 is performed on firstly the odd field and subsequently the even field, and because the accumulating operation and the pixel data transferring operation on the even field are sequentially performed vertically from top to bottom.

The above described accumulating operations of the odd field and the even field to the CCD image sensor 16 and the pixel data transferring operations on the odd field and the even field to the register 17 are repeated in sequence during the lighting duration or the shielding duration. Immediately after all the pixel data on the odd field and the even field which are obtained by a single light emission have been transferred to the register 17, all pixel data are read out of the register 17 to be input to the image processing device 18 to be decompressed into a single image frame, and this image is visually indicated on the indicating device 19 (see FIG. 5D). This pixel data readout operation is performed in synchronization with a commencement of the light-shielding duration so that the previous readout pixel data is not overwritten with the subsequent readout pixel data. The same image frame continues to be indicated on the indicating device 19 until the commencement of the subsequent light-shielding duration, and is replaced by the subsequent image frame shortly after the commencement of the subsequent light-shielding duration. Accordingly, high-quality images (moving images) can be indicated on the indicating device 19 since each image frame is composed of all the pixel data.

In the present embodiment of the electronic endoscope system, immediately after a capture button 22 (see FIG. 2) which is electrically connected to the image processing device 18 is depressed (see FIG. 5E), the image processing device 18 stops outputting image signals to the indicating device 19, and the currently indicated image on the indicating device 19 continues to be indicated as a freeze-frame image (see FIG. 5F). The image data accumulated in the register 17 continues to be read out to be input to the image processing device 18 even after the depression of the capture button 22, and the image processing device 18 resumes outputting image signals to the indicating device 19 so that the indicating device 19 sequentially indicates live images on the indicating device if the capture button 22 is again depressed.

According to the above description, an electronic endoscope system and a lighting device therefor can be achieved, the lighting device incorporating a set of small-diameter rotary shutters, which do not require a mechanism for changing the distance between the rotational axis of the set of rotary shutters and the optical axis of the lighting device, and are capable of rotating while remaining in balance.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. A lighting device for an electronic endoscope system, the lighting device comprising:
   a light source;
   a set of rotary shutters comprising at least two rotary shutters, and having a rotational axis parallel to an optical axis of said light source, said at least two rotary shutters alternately intercepting incident illuminating light emitted from said light source and allowing said incident illuminating light to pass through said set of rotary shutters toward a light guide, wherein said at least two rotary shutters are associated with each other and configured to integrally rotate about said rotational axis, each of said at least two rotary shutters having at least one light-shielding portion and at least one opening;

a first motor that integrally rotates said set of rotary shutters; and an adjusting device which rotates one of said at least two rotary shutters relative to an other of said at least two rotary shutters to change an opening angle of said at least one opening to adjust an amount of said illuminating light which passes through said set of rotary shutters, and said adjusting device including a second motor that rotates said one of said at least two rotary shutters relative to the other of said at least two rotary shutters.

2. The lighting device according to claim 1, wherein said second motor comprises an ultrasonic motor.

3. The lighting device according to claim 1, wherein each of said at least two rotary shutters has two light-shielding portions and two openings and said opening angle is changeable within a range of zero to 90 degrees.

4. The lighting device according to claim 1, wherein rotational axes of said first motor and said second motor extend coaxially.

5. The lighting device according to claim 1, wherein each of said at least two rotary shutters comprises:

a central disc portion; and two rotationally-symmetrical arc-shaped light-shielding portions and two rotationally-symmetrical arc-shaped cutout portions which are arranged at equi-angular intervals about a rotational axis of said each rotary shutter.

6. A light controller for an electronic endoscope system, the light controller comprising:

a set of rotary shutters comprising at least two rotary shutters, and having a rotational axis parallel to an optical axis of a light source, said at least two rotary shutters alternately intercepting incident illuminating light emitted from the light source and allowing said incident illuminating light to pass through said set of rotary shutters toward a light guide, wherein said at least two rotary shutters are associated with each other and configured to integrally rotate about said rotational axis, each of said at least two rotary shutters having at least one light-shielding portion and at least one opening;

a first motor that integrally rotates said set of rotary shutters, and an adjusting device which rotates one of said at least two rotary shutters relative to an other of said at least two rotary shutters to change an opening angle of said at least one opening to adjust an amount of said illuminating light which passes through said set of rotary shutters, and said adjusting device including a second motor for rotating said one of said at least two rotary shutters relative to said other of said two rotary shutters.

7. The light controller according to claim 6, wherein said second motor comprises an ultrasonic motor.

8. The light controller according to claim 6, wherein each of said at least two rotary shutters has two light-shielding portions and two openings and said opening angle is changeable within a range of zero to 90 degrees.

9. The light controller according to claim 6, wherein rotational axes of said first motor and said second motor extend coaxially.

10. The light controller according to claim 6, wherein each of said at least two rotary shutters comprises:

a central disc portion; and two rotationally-symmetrical arc-shaped light-shielding portions and two rotationally-symmetrical arc-shaped cutout portions which are arranged at equi-angular intervals about a rotational axis of said each rotary shutter.

11. An electronic endoscope system comprising:

a controller which is manually operable by an operator;

an insertion portion which extends from said controller, and configured to be inserted into an internal cavity of a subject to be inspected;

a light guide which extends through said controller and said insertion portion so that an end of said light guide extends to a distal end of said insertion portion; and a lighting device for supplying illuminating light to said light guide, wherein said lighting device comprises:

a light source which emits said illuminating light;

a set of rotary shutters comprising at least two rotary shutters, and having a rotational axis parallel to an optical axis of said light source, said at least two rotary shutters alternately intercepting incident illuminating light emitted from said light source and allowing said incident illuminating light to pass through said set of rotary shutters toward said light guide, wherein said at least two rotary shutters are associated with each other and configured to integrally rotate about said rotational axis, each of said at least two rotary shutters having at least one light-shielding portion and at least one opening;

a first motor that integrally rotates said set of rotary shutters, and an adjusting device which rotates one of said at least two rotary shutters relative to an other of said at least two rotary shutters to change an opening angle of said at least one opening to adjust an amount of said illuminating light which passes through said set of rotary shutters, and said adjusting device including a second motor for rotating said one of said at least two rotary shutters relative to said other of said at least two rotary shutters.

12. The lighting device according to claim 11, wherein said second motor comprises an ultrasonic motor.

13. The electronic endoscope system according to claim 11, wherein each of said at least two rotary shutters has two light-shielding portions and two openings and said opening angle is changeable within a range of zero to 90 degrees.

14. The electronic endoscope system according to claim 11, wherein rotational axes of said first motor and said second motor extend coaxially.

15. The electronic endoscope system according to claim 11, wherein each of said at least two rotary shutters comprises:

a central disc portion; and two rotationally-symmetrical arc-shaped light-shielding portions and two rotationally-symmetrical arc-shaped cutout portions which are arranged at equi-angular intervals about a rotational axis of said each rotary shutter.

* * * * *